United States Patent [19]

Petrillo, Jr.

[11] 4,186,268

[45] Jan. 29, 1980

[54] MERCAPTOACYLPYRROLIDINE PHOSPHONIC ACIDS AND RELATED COMPOUNDS

[75] Inventor: Edward W. Petrillo, Jr., Pennington, N.J.

[73] Assignee: E. R. Squibb & Sons, Inc., Princeton, N.J.

[21] Appl. No.: 7,131

[22] Filed: Jan. 29, 1979

[51] Int. Cl.² ............... C07D 211/36; C07D 207/10; C07D 207/46; C07D 211/92

[52] U.S. Cl. ............................. 546/21; 260/326.5 S; 424/267; 424/274

[58] Field of Search ............... 546/21; 260/326.5 S

[56] References Cited

U.S. PATENT DOCUMENTS 4,046,889  9/1977  Ondetti et al. ............... 424/274
4,105,776  8/1978  Ondetti et al. ............... 424/274

Primary Examiner—Alan L. Rotman
Assistant Examiner—Robert T. Bond
Attorney, Agent, or Firm—Lawrence S. Levinson; Burton Rodney

[57] ABSTRACT

New mercaptoacylpyrrolidine- and mercaptoacylpiperidine phosphonic acids which have the general formula

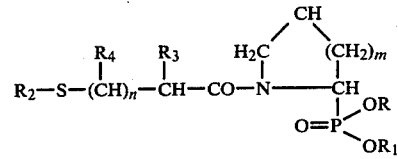

are useful as angiotensin converting enzyme inhibitors.

20 Claims, No Drawings

MERCAPTOACYLPYRROLIDINE PHOSPHONIC ACIDS AND RELATED COMPOUNDS

SUMMARY OF THE INVENTION

This invention relates to new mercaptoacylpyrrolidine- and mercaptoacylpiperidine phosphonic acid compounds which have the general formula (I)

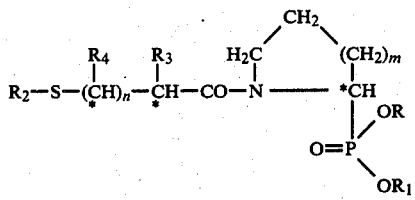

wherein

R and $R_1$ each is hydrogen, lower alkyl; phenyl-lower alkyl or a metal ion;

$R_2$ is hydrogen, lower alkanoyl, benzoyl or

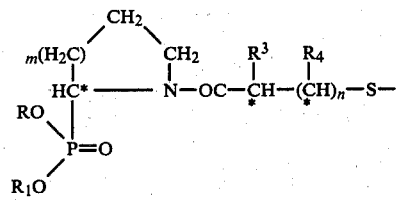

$R_3$ and $R_4$ each is hydrogen or lower alkyl;

m is 1 or 2; and n is 0 or 1.

The asterisks indicate asymmetric carbon atoms. The carbon in the acyclic side chain is asymmetric when $R_3$ and/or $R_4$ is other than hydrogen.

BACKGROUND OF THE INVENTION AND PRIOR ART

In U.S. Pat. Nos. 4,046,889 and 4,105,776, issued Sept. 6, 1977, and Aug. 8, 1978, respectively, Ondetti and Cushman have disclosed that a group of proline derivatives and related analogs which have the general formula

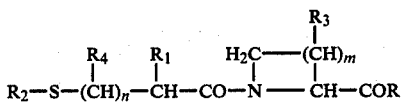

have angiotensin converting enzyme inhibiting activity and are useful as antihypertensive agents. Also in co-pending application Ser. No. 926,177, filed July 20, 1978, Ondetti and I have disclosed that a group of phosphonoacylprolines and related analogs which have the general formula

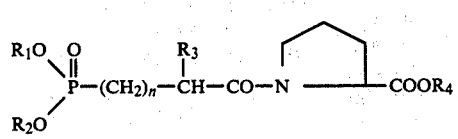

have angiotensin converting enzyme activity and are useful as antihypertensive agents too.

It has now been found that a group of new pyrrolidine and piperidine derivatives which have the general formula I have angiotensin converting enzyme inhibiting properties and they are useful as antihypertensive agents.

DETAILED DESCRIPTION OF THE INVENTION

In formula I and throughout this specification, the lower alkyl groups represented by any of the variables include straight or branched chain hydrocarbon radicals from methyl to heptyl, for example, methyl, ethyl, propyl, isopropyl, butyl, isobutyl, t-butyl, pentyl, isopentyl and the like. The $C_1$–$C_4$ members, especially $C_1$ and $C_2$ members, are preferred. Phenylmethyl is the preferred phenyl-lower alkyl group.

The lower alkanoyl groups are those having the acyl radicals of the lower ($C_2$–$C_7$) fatty acids, for example, acetyl, propionyl, butyryl, isobutyryl and the like. Similarly, those lower alkanoyl groups having up to four carbons, and especially acetyl, are preferred.

The metal ions represented by R and $R_1$ are monovalent metal ions which form metallic salts with phosphorus containing acids, e.g., alkali metal ions, especially sodium, potassium and lithium.

Preferred compounds of this invention are those compounds of formula I wherein m is 1; n is 0 or 1, especially 1; R and $R_1$ each is hydrogen, lower alkyl, especially methyl or ethyl, or alkali metal, especially sodium, potassium or lithium; $R_2$ is hydrogen or lower alkanoyl, especially acetyl; and $R_3$ and $R_4$ each is hydrogen or lower alkyl, especially methyl. Compounds in which at least one of the groups R and $R_1$ is hydrogen is especially preferred.

As indicated above, the compounds may include asymmetric carbon atoms which are designated by the asterisks and thus occur in stereoisomeric forms. The stereoisomers as well as mixtures thereof are all within the scope of the invention. Preferred are those compounds in which the cyclic portion of the molecule is in the L-form and the acyclic portion is in the D-form.

The compounds of formula I can be produced by several methods. According to one method, the free acid of the formula

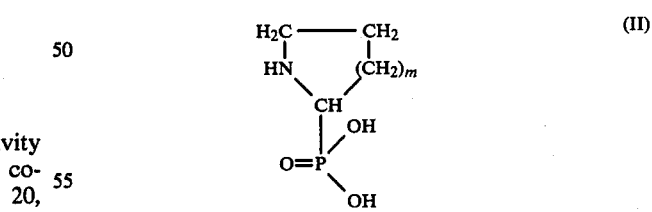

is acylated with an acyl halide of the formula

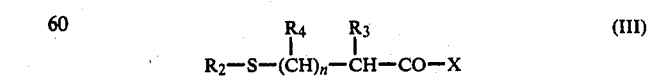

wherein X is a halogen, preferably chlorine, e.g., in the presence of a base like sodium hydroxide. $R_2$ here is hydrogen, lower alkanoyl or benzoyl.

Alternatively, a phosphonic acid ester of the formula

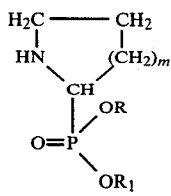

wherein R and R₁ here are other than hydrogen, is coupled with an acid of the formula

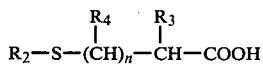

preferably in the presence of a condensing agent like 1,1'-carbonyldiimidazole or dicyclohexylcarbodiimide, in an inert organic solvent like acetonitrile, dichloromethane, ether, tetrahydrofuran, dioxane or the like. The ester group can then be removed with bromotrimethylsilane. Esters can be produced from the free acid by treating the free acid with a diazoalkane or alkyl p-tolyltriazene, e.g., with diazomethane to obtain methyl esters, or with benzyl p-tolyl triazene to obtain benzyl esters.

The acids form salts like alkali metal salts by treatment with a metal hydroxide, e.g., in aqueous medium, according to conventional methods.

The acids of formulae II and IV are derived from pyrrolidine or piperidine. Pyrrolidine or piperidine is converted to 1-pyrroline trimer or tetrahydropyridine trimer, by the methods of Y. Nomura et al., *Chem. Lett.* 693 (1977) or Grisar et al., *Synthesis*, 284 (1974), respectively. Treating the trimer with a di-lower alkylphosphite, like diethyl phosphite or di-phenyl-lower alkylphosphite like dibenzylphosphite yields the ester of formula IV. The free acid can then be derived by treating the ester with bromotrimethylsilane, or by refluxing in an aqueous mineral acid, such as hydrochloric, hydrobromic, or sulfuric acid or the like.

The acyl halides of formula III are produced by the known methods of halogenating the corresponding carboxylic acid, e.g., with thionyl chloride. See U.S. Pat. No. 4,105,776.

The disulfides, i.e., the compounds of formula I wherein R₂ is the radical

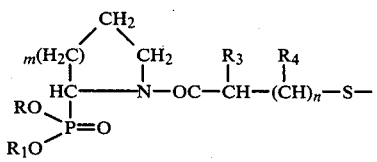

are produced by directly oxidizing with iodine a compound of formula I in which R₂ is hydrogen.

When R₂ is an acyl group, it can be converted to the compound wherein R₂ is hydrogen by treatment with a base like ammonium hydroxide, sodium hydroxide, or hydrazine hydrate.

Additional experimental details are found in the illustrative examples which are preferred embodiments and also serve as models for the preparation of other members of the group.

The compounds of this invention inhibit the conversion of the decapeptide angiotensin I to angiotensin II by angiotensin converting enzyme and therefore are useful in reducing or relieving angiotensin related hypertension, for example, renovascular hypertension or malignant hypertension. By the administration of a composition containing one or a combination of compounds of formula I or physiologically acceptable salt thereof, angiotensin dependent hypertension in the species of mammal, e.g., rats, cats, dogs, etc., suffering therefrom is reduced or alleviated. A single dose, or preferably two to four divided daily doses, provided on a basis of about 1 to 1000 mg. per kilogram per day, preferably about 10 to 200 mg. per kilogram per day is appropriate to reduce blood pressure as indicated in the animal model experiments described by S. L. Engel, T. R. Schaeffer, M. H. Waugh and B. Rubin, Proc. Soc. Exp. Biol. Med. 143, 483 (1973). The substance is preferably administered orally, but parenteral routes such as subcutaneously, intramuscularly, intravenously or intraperitoneally can also be employed.

The compounds of this invention can be utilized to achieve the reduction of blood pressure by formulating in conventional compositions such as tablets, capsules or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparation is such that a suitable dosage in the range indicated is obtained.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are illustrative of the invention and constitute preferred embodiments. All temperatures are in degrees Celsius.

EXAMPLE 1

2-Phosphonopyrrolidine (a) 1-Pyrroline trimer

1-Pyrroline trimer is prepared by the procedure of Y. Nomura et al., *Chem. Lett.* 693 (1977). Pyrrolidine (25.0 ml., 0.3 ml.), silver nitrate (0.26 gm., 0.0015 mol.) and sodium hydroxide (24.0 gm. 0.6 mol.) are dissolved in 300 ml. of water and cooled to 0°. Sodium peroxydisulfate (71.4 gm., 0.3 mol.) in 300 ml. of water is added at a rate such that the temperature does not exceed 0°. When addition is complete, the mixture is stirred for 2½ hours. The mixture is then extracted with dichloromethane and the extracts are washed with brine, dried (MgSO₄) and evaporated to a brown oil which is allowed to stand overnight in the cold, then taken up in ether and filtered to remove a black solid. The filtrate is evaporated to yield 10.7 gm. (52%) of 1-pyrroline trimer.

(b) 2-Phosphonopyrrolidine, diethyl ester

Diethyl phosphite (20.0 ml, 0.155 mol.) and 1-pyrroline trimer (10.7 gm., 0.155 mol.) are mixed under argon and heated at 85° for 90 minutes, then subjected to vacuum to remove volatiles. The residue (28 gm.) is distilled to give a main fraction, b.p. 85°–8°/0.025 mm with a recovery of 52%. $^{13}$C-nmr (CDCl$_3$): 61.0 d (J=8, ethyl CH$_2$), 53.1 d (d=164, αCH), 47.3 d (J=10, δCH$_2$) 25.8 s (γCH$_2$), 25.1 d (J=8, βCH$_2$), 15.5 d (J=5 ethyl CH$_3$).

(c) 2-Phosphonopyrrolidine

2-Phosphonopyrrolidine, diethyl ester (crude, 10.0 gm., 0.048 mol.) is refluxed in 200 ml. of 10% hydrochloric acid overnight. The black solution is evaporated in vacuo and the residue is applied to a column of AG-50W (H+) cation exchange resin. Elution with distilled water yields an initial strongly acidic fraction, then a neutral fraction, and finally a weakly acidic fraction from which the product is isolated by evaporation. Crystallization from water-ethanol gives 4.1 gm. (63%) of 2-phosphonopyrrolidine, as a crystalline solid, m.p. 275°–280°.

EXAMPLE 2

[DL-1-(3-Mercapto-1-oxopropyl)-2-pyrrolidinyl]phosphinic acid, lithium salt

(a)
[DL-1-(3-Acetylthio-1-oxopropyl)-2-pyrrolidinyl]phosphonic acid, diethyl ester 3-Acetylthiopropanoic acid is freshly crystallized from ether/hexane. This acid (7.40 gm., 0.05 mol.), 2-phosphonopyrrolidine, diethyl ester (10.35 gm., 0.05 mol.) dicyclohexylcarbodiimide (10.24 gm., 0.05 mol.) are dissolved in 300 ml. of dichloromethane and stirred 30 minutes at 0°. The cooling bath is removed and the mixture is stirred overnight. The resulting suspension is filtered and the filtrate washed with saturated sodium bicarbonate, 5% potassium bisulfate, dried (MgSO$_4$) and evaporated to a yellow oil (13.0 gm.). This oil is chromatographed on silica gel using CH$_2$Cl$_2$—CH$_2$Cl$_2$/EtOAc. A main fraction containing 10.5 gm. (62%) of [DL-1-(3-acetylthio-1-oxopropyl)-2-pyrrolidinyl]phosphonic acid, diethyl ester is collected.

(b)
[DL-1-(3-Acetylthio-1-oxopropyl)-2-pyrrolidinyl]phosphonic acid

[DL-1-(3-Acetylthio-1-oxopropyl)-2-pyrrolidinyl]phosphonic acid, diethyl ester (3.0 gm., 0.0089 mol.) is dissolved in 30 ml. dry dichloromethane, cooled to 0° under argon, and treated dropwise with bromotrimethylsilane (2.5 ml., 0.019 mol.). After stirring 4 hours, the mixture is evaporated in vacuo and the residue stirred with 30 ml. of water. The solution is washed with ether and purged with argon, then lyophilized to yield the product, [DL-1-(3-acetylthio-1-oxopropyl)-2-pyrrolidinyl]phosphonic acid, as a clear glass.

(c)
[DL-1-(3-Mercapto-1-oxopropyl)-2-pyrrolidinyl]phosphonic acid

[DL-1-(3-Acetylthio-1-oxopropyl)-2-pyrrolidinyl]phosphonic acid is dissolved in water and purged with argon. Hydrazine hydrate (1.5 ml., 0.03 mol.) is added and the mixture is stirred two hours. The solution is then applied to a column of AG-50W (H+) ion exchange resin and eluted with water. The SH-positive fractions are combined and lyophilized to yield 1.45 gm. of [DL-1-(3-mercapto-1-oxopropyl)-2-pyrrolidinyl]phosphonic acid as a clear glass.

(d)
[DL-1-(3-Mercapto-1-oxopropyl)-2-pyrrolidinyl]phosphonic acid, lithium salt

[DL-1-(3-Mercapto-1-oxopropyl)-2-pyrrolidinyl]phosphonic acid (1.45 gm.) is taken up in a minimum of water applied to a column of AG-50W (Li+) ion exchange resin and eluted with water. The SH positive fractions (pH6) are combined, millipore filtered, and lyophilized to obtain [DL-1-(3-mercapto-1-oxopropyl)-2-pyrrolidinyl]phosphinic acid, lithium salt as a white, hygroscopic solid, total 1.5 gm.

Anal: Calcd. for C$_7$H$_{13}$NO$_4$PS.Li-C, 34.30; H, 5.34; N, 5.79; S, 13.08; P, 12.63; Li, 2.83. Found: C, 34.59; H, 5.54; N, 6.08; S, 12.78; P, 12.35; Li, 2.77.

EXAMPLE 3

2-Phosphonopiperidine

(a) 2-Phosphonopiperidine, diethyl ester

Substitution of 2,3,4,5,-tetrahydropyridine trimer (prepared by the method of J. M. Grisar et al, *Synthesis* 284 (1974)) for the 1-pyrrolidine trimer in the procedure of Example 1, part (b), affords the product, 2-phosphonopiperidine, diethyl ester.

(b) 2-Phosphonopiperidine

Substitution of 2-phosphonopiperidine, diethyl ester, for the 2-phosphonopyrrolidine, diethyl ester, in the procedure of Example 1, part (c), leads to the product, 2-phosphonopiperidine.

EXAMPLE 4

[DL-1-(3-Mercapto-1-oxopropyl)-2-piperidinyl]phosphonic acid, disodium salt

(a)
[DL-1-(3-Acetylthio-1-oxopropyl)-2-piperidinyl]phosphinic acid, diethyl ester Substitution of 2-phosphonopiperidine, diethyl ester for the 2-phosphonopyrrolidine, diethyl ester in the procedure of Example 2, part (a), leads to the product, [DL-1-(3-acetylthio-1-oxopropyl)-2-piperidinyl]phosphonic acid, diethyl ester.

(b)
[DL-1-(3-Acetylthio-1-oxopropyl)-2-piperidinyl]phosphonic acid

Substitution of [DL-1-(3-acetylthio-1-oxopropyl)-2-piperidinyl]phosphonic acid, diethyl ester for the [DL-1-(3-acetylthio-1-oxopropyl)-2-pyrrolidinyl]phosphonic acid in the procedure of Example 2, part (b), leads to the product, [DL-1-(3-acetylthio-1-oxopropyl)-2-piperidinyl]phosphonic acid.

(c)
[DL-1-(3-Mercapto-1-oxopropyl)-2-piperidinyl]phosphonic acid

Substitution of [DL-1-(3-acetylthio-1-oxopropyl)-2-piperidinyl]phosphonic acid for the [DL-1-(3-acetylthio-1-oxopropyl)-2-pyrrolidinyl]phosphonic acid in the procedure of Example 2, part (c), gives the product, [DL-1-(3-mercapto-1-oxopropyl)piperidinyl]phosphonic acid.

(d)

[DL-1-(3-Mercapto-1-oxopropyl)-2-piperidinyl]phosphonic acid, disodium salt

[DL-1-(3-Mercapto-1-oxopropyl)-2-piperidinyl]phosphonic acid is dissolved in water and neutralized with two equivalents of 1 N sodium hydroxide. The resulting solution is lyophilized to obtain the product, [DL-1-(3-mercapto-1-oxopropyl)-2-piperidinyl]phosphonic acid, disodium salt.

EXAMPLE 5

[1(S),2(±)]-[1-(3-Mercapto-2-methyl-1-oxopropyl)-2-pyrrolidinyl]phosphonic acid, dipotassium salt (a)

[1(S),2(±)]-[1-(3-Acetylthio-2-methyl-1-oxopropyl)-2-pyrrolidinyl]phosphonic acid, diethyl ester Substitution of (S-)-3-acetylthio-2-methylpropanoic acid for the 3-acetyl thiopropanoic acid in the procedure of Example 2, part (a), gives the product, [1(S),2(±)]-[1-(3-acetylthio-2-methyl-1-oxopropyl)pyrrolidinyl]phosphonic acid, diethyl ester.

(b)

[1(S),2(±)]-[1-(3-Acetylthio-2-methyl-1-oxopropyl)-2-pyrrolidinyl]phosphonic acid Substitution of [1-(3-acetylthio-2-methyl-1-oxopropyl)pyrrolidinyl]phosphonic acid, diethyl ester for the [DL-1-(3-acetylthio-1-oxopropyl)pyrrolidinyl]phosphonic acid, diethyl ester in the procedure of Example 2, part (b), leads to the product, [1(S),2(±)]-[1-(3-acetylthio-2-methyl-1-oxopropyl)pyrrolidinyl]phosphonic acid.

(c)

[1(S),2(±)]-[1-(3-Mercapto-2-methyl-1-oxopropyl)-2-pyrrolidinyl]phosphonic acid

Substitution of [1(S),2(±)]-[(3-acetylthio-2-methyl-1-oxopropyl)pyrrolidinyl]phosphonic acid for the [DL-1-(3-acetylthio-1-oxopropyl)-2-pyrrolidinyl]phosphonic acid in the procedure of Example 2, part (c), leads to the product, [1(S),2(±)]-[1-(3-mercapto-2-methyl-1-oxopropyl)-2-pyrrolidinyl]phosphonic acid.

(d)

[1(S),2(±)]-[1-(3-Mercapto-2-methyl-1-oxopropyl)-2-pyrrolidinyl]phosphonic acid, dipotassium salt Substitution of 1 N potassium hydroxide for the 1 N sodium hydroxide, and of [1(S),2(±)]-[-(3-mercapto-2-methyl-1-oxopropyl)pyrrolidinyl]phosphonic acid for the [DL-1-(3-mercapto-1-oxopropyl)piperidinyl]phosphonic acid in the procedure of Example 4, part d), leads to the product, [1(S),2(±)]-[1-(3-mercapto-2-methyl-1-oxopropyl)pyrrolidinyl]phosphonic acid, dipotassium salt.

EXAMPLE 6

[DL-1-(3-Mercapto-1-oxopropyl)-2-pyrrolidinyl]phosphonic acid, dimethyl ester

A solution of [DL-1-(3-mercapto-1-oxopropyl)-2-pyrrolidinyl]phosphonic acid in ethyl acetate is treated with an excess of diazomethane in ether. The resulting solution is evaporated to give the product, [DL-1-(3-mercapto-1-oxopropyl)-2-pyrrolidinyl]phosphonic acid, dimethyl ester.

EXAMPLE 7

[DL-1-(3-Mercapto-1-oxopropyl)-2-piperidinyl]phosphonic acid, bis(phenylmethyl) ester A solution of [DL-1-(3-mercapto-1-oxopropyl)-2-piperidinyl]phosphonic acid in ethyl acetate is treated with an excess of 1-benzyl-3-p-tolyltriazene in ether. The resulting solution is washed with 5% $KHSO_4$ solution and brine, then dried over $MgSO_4$ and evaporated. The residue is chromatographed on silica gel using $CH_2Cl_2$- ethyl acetate. A main fraction containing the product, [DL-1-(3-mercapto-1-oxopropyl)-2-piperidinyl]phosphonic acid, bis(phenylmethyl) ester is collected.

EXAMPLE 8

[DL-1-(3-Acetylthio-1-oxopropyl)-2-piperidinyl]phosphonic acid, bis(phenylmethyl) ester Substitution of [DL-1-(3-acetylthio-1-oxopropyl)-piperidinyl]phosphonic acid for the [DL-1-(3-mercapto-1oxopropyl)piperidinyl]phosphonic acid in the procedure of Example 7 leads to the product, [DL-1-(3-acetylthio-1-oxopropyl)piperidinyl]phosphonic acid, bis(phenylmethyl) ester.

EXAMPLE 9

[DL-1-(3-Benzoylthio-1-oxopropyl)-2-pyrrolidinyl]phosphonic acid, diethyl ester

Substitution of 3-benzoylthiopropanoic acid for the 3-acetylthiopropanoic acid in the procedure of Example 2, part (a), leads to the product, [DL-1-(3-benzoylthio-1-oxopropyl)-2-pyrrolidinyl]phosphonic acid, diethyl ester.

EXAMPLE 10

[DL-1-(3-Benzoylthio-1-oxopropyl)-2-piperidinyl]phosphonic acid, diethyl ester

Substitution of 3-benzoylthiopropanoic acid for the 3-acetylthiopropanoic acid in the procedure of Example 4, part (a), leads to the product, [DL-1-(3-benzoylthio-1-oxopropyl)-2-piperidinyl]phosphonic acid, diethyl ester.

EXAMPLE 11

[1-(2-Acetylthio-1-oxopropyl)-2-pyrrolidinyl]phosphonic acid

2-Phosphonopyrrolidine is dissolved in water and the pH of the solution adjusted to 7 by the addition of sodium hydroxide. The solution is cooled in an ice bath, and 2-(acetylthio)propanoyl chloride is added dropwise. During the addition, the pH of the solution is maintained at 7 by the addition of 2 N sodium hydroxide. After the addition is complete, the reaction mixture is acidified to pH 2 with concentrated HCl and extracted with ethyl acetate. Drying (over $MgSO_4$) and evaporation of the extracts affords a residue of the product, [1-(2-acetylthio-1-oxopropyl)-2-pyrrolidinyl]phosphonic acid.

EXAMPLE 12

[1-(2-Mercapto-1-oxopropyl)-2-pyrrolidinyl]phosphonic acid

Substitution of [1-(2-acetylthio-1-oxopropyl)pyrrolidinyl]phosphonic acid for the [DL-1-(3-acetylthio-1-oxopropyl)pyrrolidinyl]phosphonic acid in Example 2, part (c), leads to the product, [1-(2-mercapto-1-oxo-propyl)-2-pyrrolidinyl]phosphonic acid.

EXAMPLE 13

[1-((Acetylthio)acetyl)-2-pyrrolidinyl]phosphonic acid

Substitution of (acetylthio)acetyl chloride for the 2-(acetylthio)propanoyl chloride in the procedure of Example 11 leads to the product, [1-((acetylthio)acetyl)-2-pyrrlidinyl]phosphonic acid.

EXAMPLE 14

[1-((Acetylthio)acetyl)-2-piperidinyl]phosphonic acid

Substitution of 2-phosphonopiperidine for the 2-phosphonopyrrolidine in the procedure of Example 13 leads to the product, [1-((acetylthio)acetyl)-2-piperidinyl]phosphonic acid.

EXAMPLE 15

[1-(Mercaptoacetyl)-2-piperidinyl]phosphonic acid

Substitution of [1-((acetylthio)acetyl)-2-piperidinyl]phosphonic acid for the [DL-1-(3-acetylthio-1-oxopropyl)-2-pyrrolidinyl]phosphonic acid in the procedure of Example 2, part (c), leads to the product, [1-(mercaptoacetyl)-2-piperidinyl]phosphonic acid.

EXAMPLE 16

[1-(3-Acetylthio-2-ethyl-1-oxopropyl)-2-pyrrolidinyl]phosphonic acid

Substitution of 3-acetylthio-2-ethyl propanoyl chloride for the 2-(acetylthio)propanoyl chloride in the procedure of Example 11 leads to the product, [1-(3-acetylthio-2-ethyl-1-oxopropyl)-2-pyrrolidinyl]phosphonic acid.

EXAMPLE 17

[1-(3-Acetylthio-1-oxobutyl)-2-piperidinyl]phosphonic acid, diethyl ester

Substitution of 3-(acetylthio)butanoic acid for the 3-acetylthiopropanoic acid in the procedure of Example 4, part (a), leads to the product, [1-(3-acetylthio-1-oxobutyl)-2-piperidinyl]phosphonic acid, diethyl ester.

EXAMPLE 18

[1-(3-Acetylthio-1-oxobutyl)-2-piperidinyl]phosphonic acid

Substitution of [1-(3-acetylthio-1-oxobutyl)-2-piperidinyl]phosphonic acid, diethyl ester for the [DL-1-(3-acetylthio-1-oxopropyl)-2-pyrrlidinyl]phosphonic acid in the procedure of Example 2, part (b), leads to the product, [1-(3-acetylthio-1-oxobutyl)-2-piperidinyl]phosphonic acid.

EXAMPLE 19

[1-(3-Acetylthio-2-methyl-1-oxobutyl)-2-pyrrolindinyl]phosphonic acid

Substitution of 3-acetylthio-2-methyl butanoyl chloride for the 2-(acetylthio)propanoyl chloride in the procedure of Example 11 leads to the product, [1-(3-acetylthio-2-methyl-1-oxobutyl)-2-pyrrolidinyl]phosphonic acid.

EXAMPLE 20

1,1'-[Dithiobis(1-oxo-3,1-propanediyl)]bis(2,1-pyrrolidinediyl)diphosphonic acid

[DL-1-(3-Mercapto-1-oxopropyl)-2-pyrrolidinyl]phosphinic acid is dissolved in water and the pH adjusted to 6.5 with 2 N sodium hydroxide solution. A 0.5 N solution of iodine is added dropwise, the pH being kept at 6.0–7.0 during the addition by simultaneous addition of 2 N sodium hydroxide. When the iodine color persists, the solution is applied to a column of AG-50W (H+)cation exchange resin. Elution with distilled water yields an initial strongly acidic fraction, then a weakly acidic fraction from which the product, 1,1'-[dithiobis(1-oxo-3,1-propanediyl)]bis(2,1-pyrrolidinediyl)diphosphonic acid, is isolated by lyophilization.

EXAMPLE 21

1,1'-[Dithiobis((S)2-methyl-1-oxo-3,1-propanediyl)]bis((±)2,1-pyrrolidinediyl)diphosphonic acid Substitution of [1(S),2(±)]-[1-(3-mercapto-2-methyl-1-oxopropyl)-2-pyrrolidinyl]phosphonic acid for the [DL-1-(3-mercapto-1-oxopropyl)-2-pyrrolidinyl]phosphonic acid in the procedure of Example 20 leads to the product, 1,1'-[dithiobis(2-methyl-1-oxo-3,1-propanediyl)]bis(2,1-pyrrolidinediyl)diphosphonic acid.

EXAMPLE 22

1,1'-[Dithiobis(1-oxo-3,1-propanediyl)]bis(2,1-piperidinediyl)diphosphonic acid

Substitution of [DL-1-(3-mercapto-1-oxopropyl)-2-piperidinyl]phosphonic acid for the [DL-1-(3-mercapto-1-oxopropyl)-2-pyrrolidinyl]phosphonic acid in the procedure of Example 20 leads to the product, 1,1'-[dithiobis(1-oxo-3,1-propanediyl)]bis(2,1-piperidinediyl)diphosphonic acid.

What is claimed is:

1. A compound of the formula $$R_2-S-(CH)_n-\underset{R_3}{\overset{R_4}{CH}}-CO-N\underset{CH}{\overset{H_2C}{\diagup}}\underset{(CH_2)_m}{\overset{CH}{\diagdown}}$$
$$O=P\underset{OR_1}{\overset{OR}{\diagdown}}$$

wherein R and R$_1$ each is hydrogen, lower alkyl, phenyl-lower alkyl or an alkali metal ion;

R$_2$ is hydrogen, lower alkanoyl, benzoyl or $$m(H_2C)\underset{HC}{\overset{CH_2}{\diagup}}\underset{}{\overset{CH_2}{\diagdown}}N-OC-\underset{R_3}{\overset{}{CH}}-(CH)_n-S-$$
$$RO\diagdown P=O$$
$$R_1O\diagup$$

R$_3$ and R$_4$ each is hydrogen or lower alkyl; 
m is 1 or 2; and 
n is 0 or 1.

2. A compound as in claim 1 wherein m is 1.
3. A compound as in claim 1 wherein m is 2.
4. A compound as in claim 1 wherein R and R$_1$ are both hydrogen.

5. A compound as in claim 1 wherein R and $R_1$ are both lower alkyl.

6. A compound as in claim 1 wherein R and $R_1$ are both alkali metal.

7. A compound as in claim 1 wherein $R_2$ is hydrogen.

8. A compound as in claim 1 wherein $R_2$ is

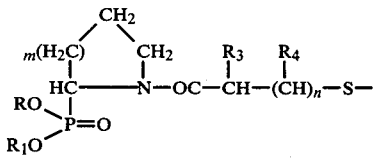

9. A compound as in claim 2 wherein n is 0 or 1; R and $R_1$ each is hydrogen, lower alkyl or alkali metal; $R_2$ is hydrogen or lower alkanoyl; and $R_3$ and $R_4$ each is hydrogen or lower alkyl.

10. A compound as in claim 2 wherein R and $R_1$ each is lower alkyl; $R_2$ is lower alkanoyl; $R_3$ and $R_4$ each is hydrogen; and n is 1.

11. A compound as in claim 10 wherein each lower alkyl group is ethyl and the lower alkanoyl group is acetyl.

12. A compound as in claim 2 wherein R, $R_1$, $R_2$, $R_3$ and $R_4$ each is hydrogen and n is 1.

13. Lithium salt of the compound of claim 12.

14. A compound as in claim 2 wherein R, $R_1$, $R_2$ and $R_4$ each is hydrogen, $R_3$ is lower alkyl and n is 1.

15. A compound as in claim 14 wherein the lower alkyl group is methyl.

16. A compound as in claim 8 where m is 1.

17. A compound as in claim 3 wherein R, $R_1$, $R_2$ and $R_4$ each is hydrogen; $R_3$ is lower alkyl; and n is 1.

18. A compound as in claim 3 wherein the lower alkyl group is methyl.

19. A compound as in claim 3 wherein R, $R_1$, $R_2$, $R_3$ and $R_4$ each is hydrogen and n is 1.

20. A compound as in claim 2 wherein R, $R_1$, $R_2$ and $R_4$ each is hydrogen, $R_3$ is methyl and n is 1.

* * * * *

UNITED STATES PATENT AND TRADEMARK OFFICE
CERTIFICATE OF CORRECTION

PATENT NO. : 4,186,268

DATED : January 29, 1980

INVENTOR(S) : Edward W. Petrillo, Jr.

It is certified that error appears in the above-identified patent and that said Letters Patent are hereby corrected as shown below:

Column 7, line 51, "[-(3-" should read --[1-(3--.
Column 8, line 22, "loxopropyl" should read --1-oxopropyl--.
Column 9, line 10, "pyrrlidinyl" should read --pyrrolidinyl--.
Column 9, line 54, "pyrrlidinyl" should read --pyrrolidinyl--.
Column 9, line 61, "pyrrolin" should read --pyrroli--.

Signed and Sealed this

Sixth Day of May 1980

[SEAL]

Attest:

SIDNEY A. DIAMOND

Attesting Officer

Commissioner of Patents and Trademarks